US008235045B2

(12) United States Patent
Moore (10) Patent No.: US 8,235,045 B2
(45) Date of Patent: Aug. 7, 2012

(54) FOREHEAD AND NOSE BRIDGE PAD FOR CPAP INTERFACE (75) Inventor: Karen Leigh Moore, Stanardsville, VA (US)

(73) Assignee: Karen Leigh Moore, Stanardsville, VA (US)

( * ) Notice: Subject to any disclaimer, the term of this patent is extended or adjusted under 35 U.S.C. 154(b) by 839 days.

(21) Appl. No.: 12/288,271

(22) Filed: Oct. 17, 2008

(65) Prior Publication Data
US 2009/0107507 A1 Apr. 30, 2009

Related U.S. Application Data (60) Provisional application No. 60/999,199, filed on Oct. 17, 2007.

(51) Int. Cl.
A62B 18/08 (2006.01)
A41D 27/26 (2006.01)
A42B 3/00 (2006.01)

(52) U.S. Cl. .................. 128/206.24; 128/207.11; 2/267; 2/414

(58) Field of Classification Search ............. 128/206.24, 128/206.21, 206.23, 206.25, 206.26, 207.11, 128/207.13, 207.17; 2/9, 173, 267, 268, 2/272, 411, 424, 460, 452, 446, 428, 414, 2/182.1, 182.2, 182.3, 181, 207; 602/41–79
See application file for complete search history.

(56) References Cited

U.S. PATENT DOCUMENTS

| 4,023,212 A | * | 5/1977 | Huffman | 2/195.2 |
| 4,472,838 A | * | 9/1984 | Pompa | 2/460 |
| 4,608,047 A | * | 8/1986 | Mattingly | 604/387 |
| 4,643,398 A | * | 2/1987 | Vetter | 254/93 HP |
| 4,944,310 A | | 7/1990 | Sullivan | |
| 4,947,488 A | * | 8/1990 | Ashinoff | 2/181 |
| 5,105,476 A | * | 4/1992 | Cox | 2/12 |
| 5,117,819 A | | 6/1992 | Servidio et al. | |
| 5,243,971 A | | 9/1993 | Sullivan et al. | |
| 5,570,689 A | | 11/1996 | Starr et al. | |
| 5,657,752 A | | 8/1997 | Landis et al. | |
| 5,724,965 A | | 3/1998 | Handke et al. | |
| 5,746,201 A | | 5/1998 | Kidd | |
| 5,887,587 A | | 3/1999 | Groenke | |
| 6,112,746 A | | 9/2000 | Kwok et al. | |
| 6,119,693 A | | 9/2000 | Kwok et al. | |
| D439,326 S | | 3/2001 | Hecker et al. | |
| D441,860 S | | 5/2001 | Kopacko et al. | |
| 6,412,487 B1 | | 7/2002 | Gunaratnam | |
| D464,727 S | | 10/2002 | Austin et al. | |

(Continued)

Primary Examiner — Steven Douglas
Assistant Examiner — Valerie L Skorupa (57) ABSTRACT The invention is a method for padding CPAP face and full face masks forehead and nose bridge area to prevent skin irritation, discomfort, indentions, allergies and ulcers. The pad is attached to the forehead part of the CPAP face mask by way of pockets sewn into the body of the pad. The pad protects the forehead area of the wearer as well as the nose bridge by way of a flap of material that fits between the seal of the mask and the wearer's nose bridge area distributing the pressure from the mask seal.
Persons with sleep apnea rely on CPAP therapy to prevent the obstruction in order to continue to breathe while sleeping. The CPAP masks appear medical and strange, especially to a new user of the device. By making the CPAP mask more comfortable with soft padding and also preventing marks and sores, it is more likely that the person will continue their therapy and improve their health. The invention is designed to be colorful, soft and comforting to help people with sleep apnea continue to get the necessary therapy.

18 Claims, 5 Drawing Sheets

U.S. PATENT DOCUMENTS

| | | |
|---|---|---|
| 6,467,483 B1 | 10/2002 | Kopacko et al. |
| 6,520,182 B1 | 2/2003 | Gunaratnam |
| 6,625,820 B1 * | 9/2003 | Lampe ............... 2/425 |
| 6,860,269 B2 | 3/2005 | Kwok et al. |
| 7,210,481 B1 | 5/2007 | Lovell et al. |
| 7,219,670 B2 | 5/2007 | Jones, Jr. et al. |
| D545,960 S | 7/2007 | Fu et al. |
| 7,243,650 B2 | 7/2007 | Thornton |
| 7,296,574 B2 | 11/2007 | Ho et al. |
| D567,935 S | 4/2008 | Fu et al. |
| D576,271 S | 9/2008 | Gunaratnam et al. |
| 2004/0025882 A1 * | 2/2004 | Madaus et al. ........... 128/206.27 |
| 2006/0021104 A1 * | 2/2006 | Weissman ............................. 2/9 |
| 2006/0081251 A1 * | 4/2006 | Hernandez et al. ...... 128/206.21 |
| 2008/0216214 A1 * | 9/2008 | Dolby ............................... 2/410 |
| 2010/0199992 A1 * | 8/2010 | Ho et al. .................. 128/205.25 |

* cited by examiner

FIG. 1

Prior Art

FOREHEAD AND NOSE BRIDGE PAD FOR CPAP INTERFACE

CROSS-REFERENCE TO RELATED APPLICATIONS

This application claims the priority, under 35 U.S.C. Sec. 119, of the U.S. Provisional Patent Application Ser. No. 60/999,199 filed Oct. 17, 2007 by the present inventor. The entire disclosures of this prior application are hereby incorporated by reference in its entirety.

STATEMENT REGARDING FEDERALLY SPONSORED RESEARCH OR DEVELOPMENT

Not Applicable

STATEMENT REGARDING SEQUENCE LISTING OR PROGRAM

Not Applicable

FIELD OF THE INVENTION

This invention relates generally to the field of respiration, or breathing and/or ventilation masks. In particular, the invention relates to the forehead portion and seal of masks used in the treatment of sleep apnea.

BACKGROUND

Prior Art

Obstructive sleep apnea syndrome (commonly referred to as obstructive sleep apnea, OSA, and/or sleep apnea) is a medical condition that has as one symptom repeated prolonged episodes of cessation of breathing throughout the night. This is generally a condition in which a person's airway becomes blocked or restricted due to the over-relaxation of the muscles and tissues in the throat during sleep. A restrictive air supply impairs the oxygen flow to the lungs and, in turn, to the brain.

An individual with OSA can stop breathing, or suffer an apnea, for many times (typically from 10 to 30 times an hour) each night. The apneas are generally followed by sudden reflexive attempts to breathe. As a result, the individual suffering from OSA experiences fragmented sleep. Such non-refreshing sleep results in daytime drowsiness, headaches, weight gain, limited attention span, memory loss, lethargy, inability to maintain concentration and/or depression. OSA has also been linked to increased hypertension and greater risk of stroke, heart disease, and diabetes if left untreated. Untreated sleep apnea is also a leading cause of automobile accidents.

Effective treatment requires the airway to remain open during sleep. Modern respiratory therapy utilizes a "continuous positive airway pressure" (CPAP) machine and a ventilation interface during sleep in order to keep the airways open. A variety of CPAP machines can provide this treatment. BiPAP and VPAP are two specialized examples of CPAP machines that vary the pressure received based on the patient's breathing patterns. All positive airway pressure machines use an interface to deliver ambient air, under pressure, to the patient's airway which effectively forms a splint for the trachea. This interface usually consists of a nasal mask, full face mask (covering both the nose and mouth), or nasal pillows held onto the patient's face with straps, or headgear, and connected to the CPAP machine by way of an air hose. The nasal mask and full face mask employ a forehead pad that rests against the patient's forehead to stabilize the mask and to position the mask seal over the nose.

No matter what type of OSA interface is used, holding it in place over the nose and/or mouth is difficult, due to the air pressure blowing into it. The interface must be held in place securely to prevent air from escaping around the seal. The structure of the interface also must be rigid, and at the same time, soft against the wearer's skin. The mask seal against the bridge of the nose can cause pressure ulcers or bruising. When this is unresolved, it can be a major deterrent for the user to continue CPAP therapy.

Another difficulty results in the psychological aspects of the treatment. The CPAP and mask must be used anytime the person sleeps, including naps, for the duration of the patient's life in order to be effective against the long-lasting dangers of OSA. The mask and headgear is unnatural, cumbersome, medical, uncomfortable as well as unattractive on the face. CPAP treatment has even been the cause of personal relationships being destroyed. The hospital look of the mask during use, and the marks remaining on the face after use are a continual reminder of the patient's medical condition.

As a result of the varieties of difficulties and discomfort, some patients remove their masks in the night, at times not having realized that they have done so. Some patients choose to discontinue treatment for OSA because of the many difficulties associated with adjusting to the CPAP masks and nightly treatment. Without treatment compliance, OSA progressively becomes more severe as a person ages.

Durable Medical Equipment Suppliers (DME) have limited style choices available in masks and CPAP machines for the patients. Most of the masks and headgear are very similar in appearance and structure. Most patients have little knowledge about OSA when they are diagnosed and know very little about the treatment options. The patients are further handicapped due to the very nature of the disorder, and cannot think as clearly before as after receiving proper treatment, so are often given the mask and machine the DME selects for them. Having little input in the choice of equipment can negatively affect the dedication the patient has toward the treatment, especially considering the variety of challenges it presents and the extended time required to feel the benefits of the therapy, often taking a month or longer.

The invention of a colorful, very soft, forehead and nose bridge protection alleviates parts of the problems with OSA therapy listed above and helps patients remain compliant with their treatment. Compliant treatment allows the patients to experience a much greater quality and length of life.

In the related art, numerous attempts at treatment of OSA have been made. These attempts have included new masks and headgear designs; some have included designs to reduce the amount of contact area against the skin. Although the present style of masks include a forehead part, they do not address adequately the marks and bruising caused by the forehead part as well as the seal where it contacts the patient's nose bridge. A search of the prior art did not disclose any patents that read directly on the claims of the invention herein disclosed, however, the following patents were considered relevant:

| U.S. Pat. No. | Inventor | Issue Date |
| --- | --- | --- |
| 4,944,310 | Colvin E. Sullivan | Jul. 31, 1990 |
| 5,177,819 | Servidio et al | Jun. 2, 1992 |

-continued

| U.S. Pat. No. | Inventor | Issue Date |
|---|---|---|
| 5,243,971 | Sullivan et al | Sep. 14, 1993 |
| 5,570,689 | Starr et al | Nov. 5, 1996 |
| 5,657,752 | Landis et al | Aug. 19, 1997 |
| 5,746,201 | Lisa A. Kidd | May 5, 1998 |
| 5,724,965 | Handke et al | Mar. 10, 1998 |
| 5,887,587 | Allen W. Groenke | Mar. 30, 1999 |
| 6,122,746 | Kwok et al | Sep. 5, 2000 |
| 6,199,693 | Kwok et al | Sep. 19, 2000 |
| D441,860 S | Kopacko et al | May 8, 2001 |
| D439,326 S | Hecker et al | Mar. 20, 2001 |
| 6,412,487 B1 | Gunaratnam | Jul. 2, 2002 |
| 6,467,483 B1 | Kopacko et al | Oct. 22, 2002 |
| D464,727 S | Austin et al | Oct. 22, 2002 |
| 6,520,182 B1 | Gunaratnam | Feb. 16, 2003 |
| 6,860,269 B2 | Kwok et al | Mar. 1, 2005 |
| 7,210,481 B1 | Lovell et al | May 1, 2007 |
| 7,219,670 B2 | Jones, Jr. et al | May 22, 2007 |
| D545,960 S | Fu et al | Jul. 3, 2007 |
| 7,243,650 B2 | W. Keith Thornton | Jul. 17, 2007 |
| 7,296,574 B2 | Peter Ho et al | Nov. 20, 2007 |
| D567,935 S | Fu et al | Apr. 29, 2008 |
| D576, 271 | Gunaratnam et al | Sep. 2, 2008 |

BACKGROUND

Objects and Advantages

While there are devices that provide treatment options for OSA, these do not disclose a successful padding solution for the CPAP interfaces. In this respect, the nasal headgear padding described herein departs from any present designs in providing comfort, physically and mentally, and style. Compliancy improves dramatically when the patient has comfortable options for the treatment of OSA.

The present invention, (Forehead and Nose Bridge Pad for CPAP Interface) discloses a padding which covers the CPAP forehead pad on the mask adjacent to the face. It also includes padding to prevent pressure ulcers on the nose bridge area. This extremely soft pad protects the wearer's forehead and bridge of the nose from any irritation caused by the presence of the interface. The present invention also protects the facial skin from any allergic reaction to the materials of the forehead part of the mask by forming a physical barrier. The material of the present invention is such that it promotes air circulation under the forehead pad controlling moisture build up and discomfort. The present invention provides distribution of the pressure applied by the mask to the skin in the areas of the forehead as well as the area of the bridge of the nose. By padding the edge of the forehead pad of the mask, the present invention prevents lasting indentions from forming on the forehead, and the flap portion prevents bruising and sores on the nose bridge. The softness of the present invention is comparable to a very soft blanket against the forehead and nose bridge adding physical as well as psychological comfort to the treatment of OSA. Soft comfortable padding increases the ease of falling to sleep and staying asleep.

The present invention (Forehead and Nose Bridge Pad for CPAP Interface) discloses that padding the forehead and nose bridge and preventing facial marks and sores allow the wearer of the CPAP mask to only think about the treatment of OSA at night when going to bed. It allows the medical nature of the disorder to be a private matter instead of having to explain the marks or sores on the face left behind by the interface at night. Psychological benefits include a more positive self image, and improve social interaction. The present invention improves the outward medical appearance of the headgear by being colorful and very soft as well as personalized. It also allows individual style for each person by being available in many colors. The present invention can match other clothing worn to bed and feel more like an accessory.

The present invention can be changed often when the wearer wants a different style or color on the headgear.

The present invention (Forehead and Nose Bridge Pad for CPAP Interface) discloses that by adding padding to certain non-adjusting forehead parts, it effectively reduces the pressure of the mask seal on the wearer's face.

Prior art treatment options for OSA do not adequately address a successful padding solution for the headgear of CPAP interfaces. The Forehead and Nose Bridge Pad for CPAP Interface padding described herein deviates from any prior art in providing improvements in the way of comfortable options for OSA patients and thereby improves compliancy. Still further objects and advantages will become apparent from a consideration of the ensuing description and drawings.

SUMMARY

In accordance with the present invention, Forehead and Nose Bridge Pad for CPAP Interface, the padding for CPAP interfaces comprise a resilient, sufficiently bulky fabric formed in a fashion to provide secure padding protection for the skin on the forehead and nose bridge of a sleep apnea patient receiving CPAP therapy. This padding invention increases comfort, prevents marks and bruising on the forehead and nose bridge for patients using a CPAP mask. By offering a colorful addition to the CPAP mask, this also can add some personalization to the interface. Any improvement to OSA therapy can help patients remain compliant with their therapy which ultimately results in improved health.

DRAWINGS

Figures

| DRAWINGS: Reference Numerals: | |
|---|---|
| 21 | Decorative side of the material making up the nose bridge flap |
| 22 | Decorative side of the material making up the forehead padding body |
| 23 | Terminal ends fold in exterior decorative fabric |
| 24 | Stitching line securing the fabric in the shape to work properly |
| 25 | Lateral fold in exterior decorative fabric |
| 26 | Padding in the interior of the invention |
| 27 | Wrong side of the exterior fabric |
| 28 | Broken line showing the fabric beneath the surface |
| 29 | Notches cut from the rectangle to form the shape needed to make the invention |
| 30 | Flap portion of dense material single thickness |
| 31 | Portion of the original shape that is folded over the padding layer to form pocket |
| 32 | Slit cut along the lateral fold to accommodate straps |

-continued

DRAWINGS: Reference Numerals:

| | |
|---|---|
| 33 | Forehead part of typical CPAP mask, hidden under pad exterior |
| 34 | Seal of typical CPAP mask |
| 35 | Straps of typical CPAP mask |
| 36 | Nose bridge protector flap tucked under the seal |
| 37 | Hidden portion of the edge forming the receiving pocket of the pad |
| 38 | Pocket to receive forehead part of CPAP mask |

DETAILED DESCRIPTION OF DRAWINGS

Figure 1:
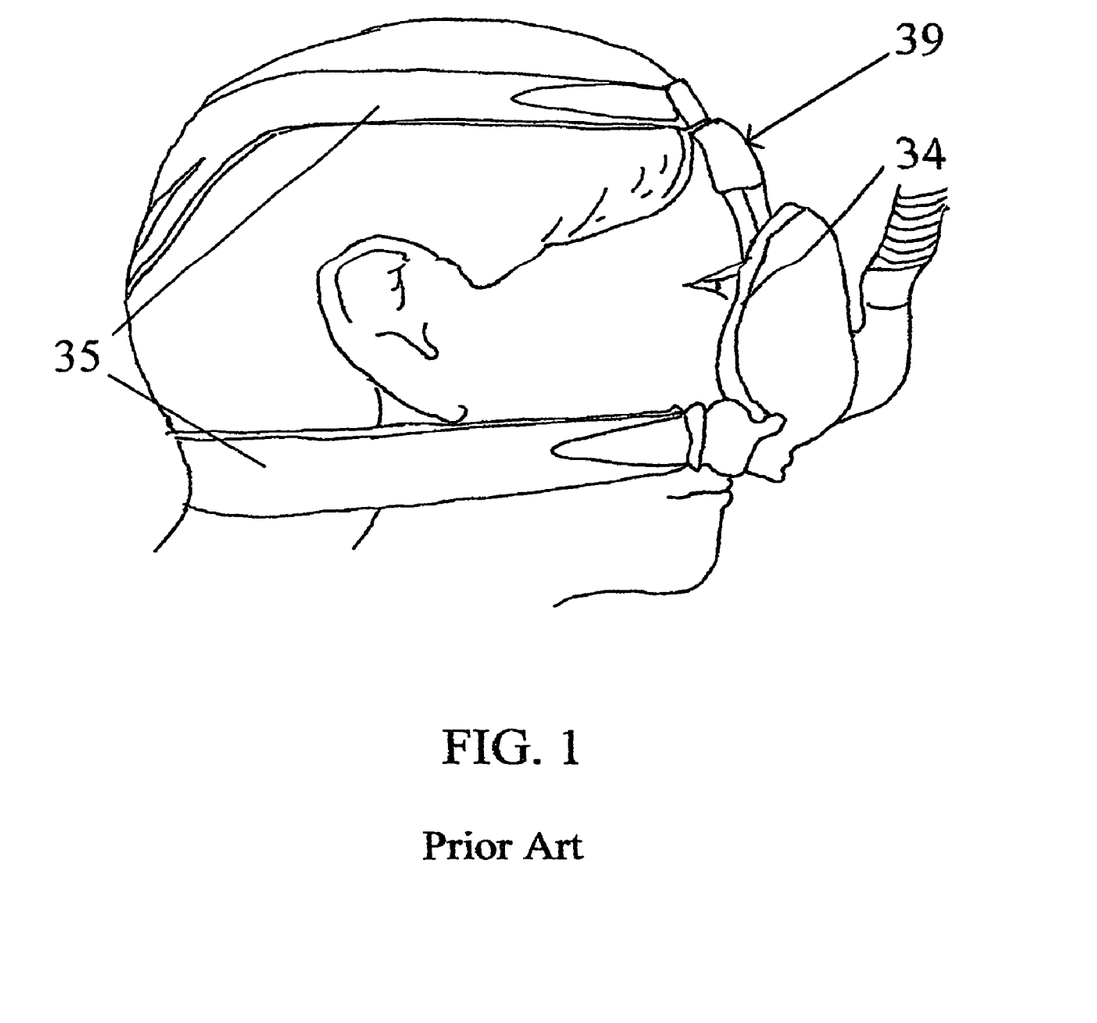
FIG. 1 shows Prior Art example of facial CPAP mask and the conventional forehead part.

FIG. 1 shows a prior art example of the conventional CPAP facial mask with integral forehead pad 39 with straps 35 which are used to secure the mask and to preserve the seal 34 against the wearer's face.

Figure 2:
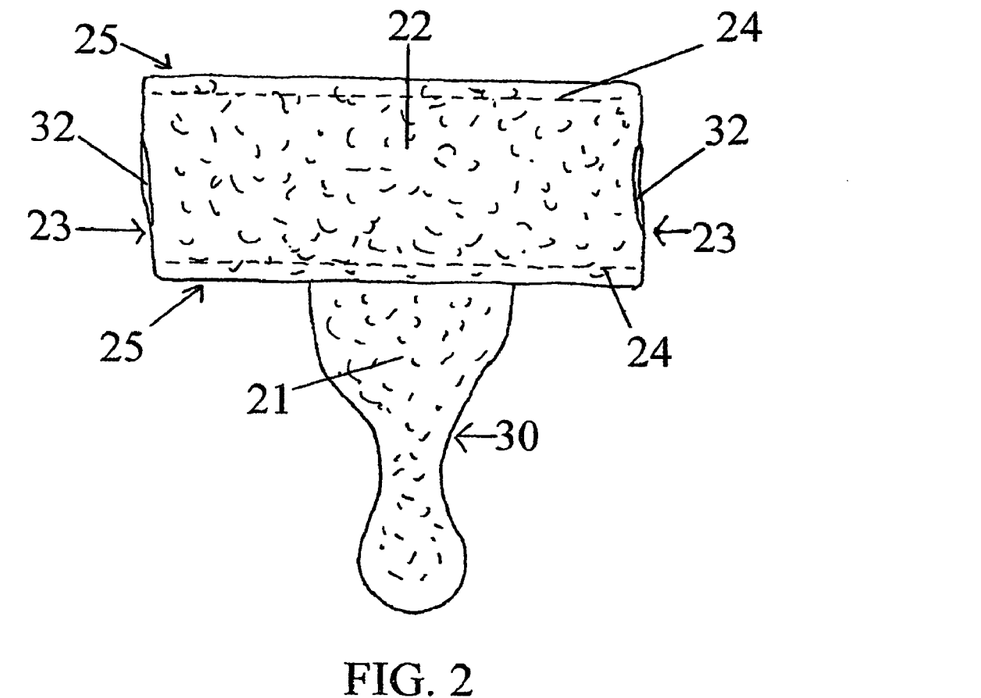
FIG. 2 shows the front view of the present invention.

FIG. 2 shows the front view of the present invention, Forehead and Nose Bridge Pad for CPAP Interface, which is intended to cover the forehead part 39 on the mask in FIG. 1. In the preferred embodiment, the forehead pad FIG. 2 is constructed of fabric material. While any fabric can be used, thin polyester micro fleece is preferred because of its soft outer surface 22 and tendency to remain completely free from raveling when cut, so as to remain un-hemmed in the application.

Figure 3:
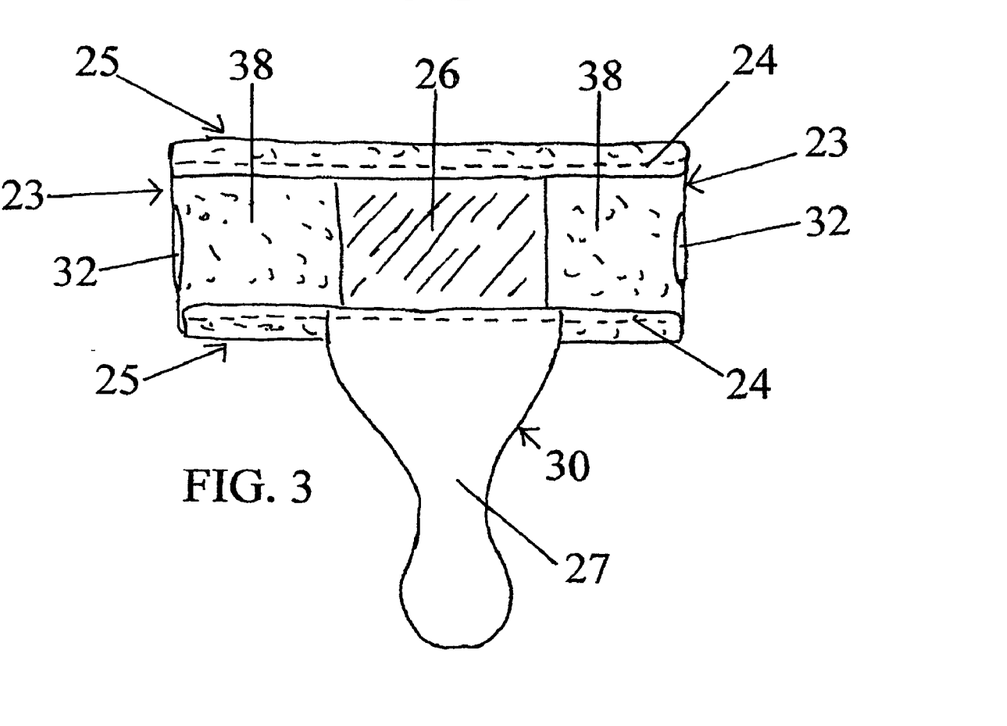
FIG. 3 shows the back view of the present invention.

FIG. 3 shows the rear view of the present invention revealing the pockets 38 for attachment to the forehead part of the mask 39, and the padding layer 26. FIG. 3 further details the stitching line 24 that secures the folded fabric into a shape to attach to the forehead part of the CPAP mask. Also FIG. 3 shows the slits 32 through the distal end folds 23 of the main forehead pad which the straps 35 may extend for certain masks to effect the stable attachment of the invention on said mask. FIG. 3 further details the nose bridge protector flap 30 size and shape in relation to the main forehead portion of the invention. The stitching line 24 secures both the sides of the invention 25 and the attached nose bridge protector flap 30.

Figure 4:
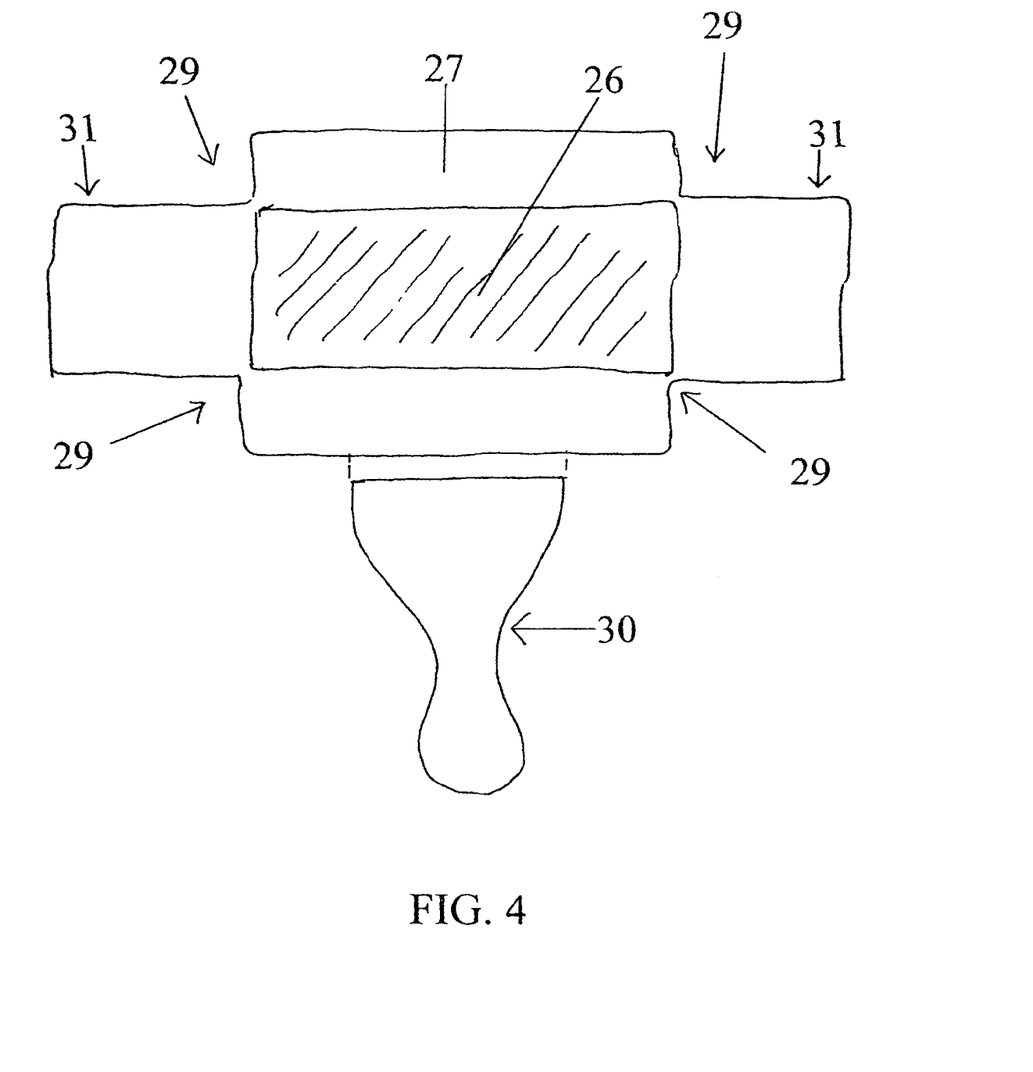
FIG. 4 shows the cutting diagram before construction.

FIG. 4 shows the approximate shape of the cut pieces of fabric making up the invention before construction. FIG. 4 shows the padding layer 26 and the placement of this on the exterior fabric. The notches 29 in the exterior fabric are to reduce the bulk when the edges are folded around the padding layer 26 during the construction. The flap piece 30 is attached after the edges of the exterior fabric are folded up.

Figure 5A:
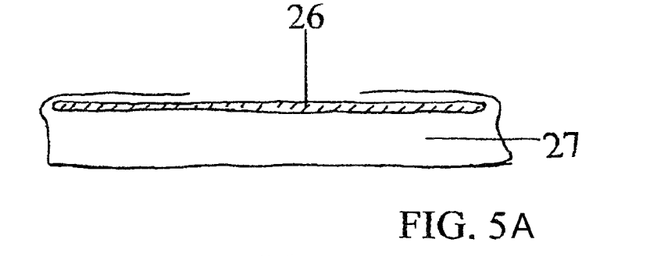
FIGS. 5A-5C show the construction process in steps.
Figure 5B:
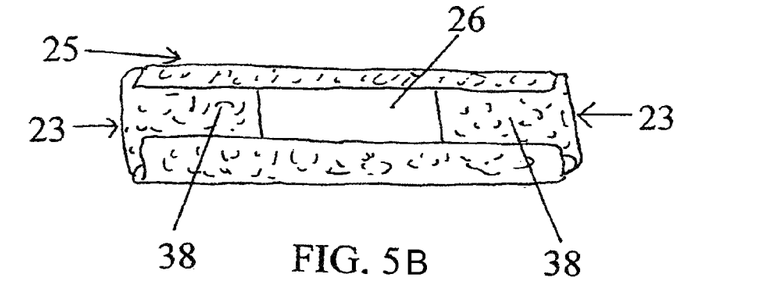
Figure 5C:
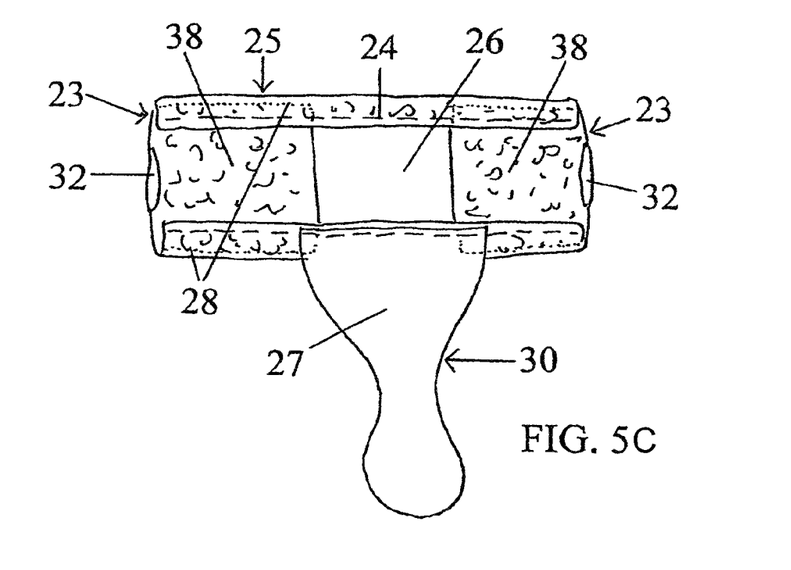

FIGS. 5A-5C show the steps in constructing the invention including the formation of the folds 23 in the distal ends. The flap on the long sides form folds 25 and overlap the end flaps 31 on FIG. 4 forming pockets on both ends of the main forehead pad. FIG. 5C further shows the stitching line 24 securing the edges of the pocket 38 as well as the flap 30 attachment. FIG. 5C also shows the slits 32 that allow certain styles of masks straps 35 to secure this invention on that style mask. FIG. 5C further shows the hidden edges 28 of the fabric under the lateral folded edge 25 and the method in which it is secured with the stitching line 24.

Figure 6:
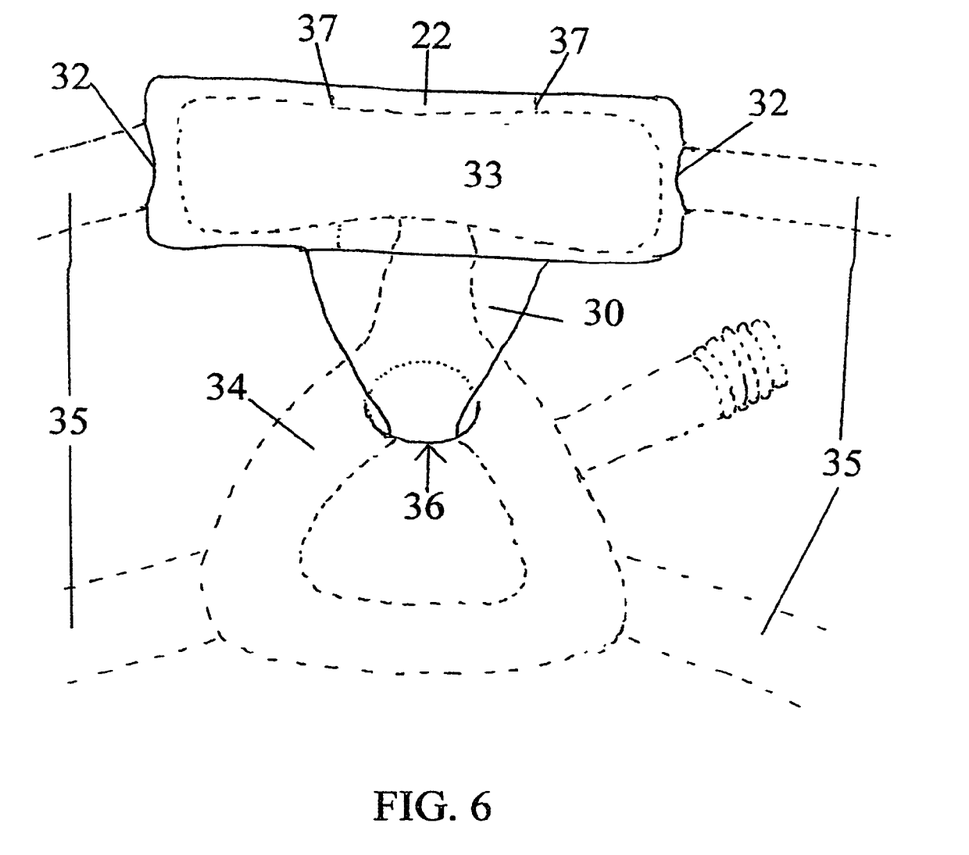
FIG. 6 shows the invention installed on a typical CPAP mask.

FIG. 6 shows the installation of the Forehead and Nose Bridge Pad for CPAP Interface on a typical CPAP mask and the method of providing padding for the wearer. FIG. 6 shows with dotted lines the CPAP mask that is improved by this invention. The mask itself is not part of this invention. FIG. 6 demonstrates the hidden edge of the pockets 37 that fit over the forehead part of the mask 33 with the slits 32 accommodating the mask straps 35. Furthermore, FIG. 6 demonstrates the nose bridge flap 30 installed tucked into the mask seal 34 providing padding on the seal that causes bruises or ulcers on the user's nose bridge.

I claim:

1. A padding for a CPAP interface to cover a forehead part on a CPAP mask, said padding comprising:
   a forehead pad comprising:
   an exterior fabric material comprising distal ends, a slit in each of said distal ends, long sides extending between said distal ends, with corner notches in said exterior fabric material to form end flaps and long flaps extending between said end flaps, wherein said end flaps are folded to form opposing pockets at said ends and an opening therebetween, and said long flaps are folded to overlap at least portions of said end flaps, and wherein said notches reduce bulk exterior fabric material where said flaps are folded, and further wherein said slits in said distal ends of said exterior fabric material extend along said folds of said end flaps, said slits allowing mask straps of the CPAP mask to pass therethrough, and further through said pockets secure the forehead pad to the CPAP mask, and
   an interior padding layer, said flaps being folded around said interior padding layer so that said interior padding layer is within said exterior fabric material.

2. A padding for a CPAP interface to cover a forehead part on a CPAP mask, said padding comprising:
   a forehead pad comprising:
   an exterior fabric material comprising distal ends, long sides extending between said distal ends, with corner notches in said exterior fabric material to form end flaps and long flaps extending between said end flaps, wherein said end flaps are folded to form opposing pockets at said ends and an opening therebetween, and said long flaps are folded to overlap at least portions of said end flaps, and wherein said notches reduce bulk exterior fabric material where said flaps are folded, and
   an interior padding layer, said flaps being folded around said interior padding layer so that said interior padding layer is within said exterior fabric material, and
   a downwardly depending nose bridge protector flap formed of a fabric material attached to a lower edge of the forehead pad along a lower one of said long flaps and extending between said end flaps, said nose bridge protector flap being sized and configured to tuck into a mask seal of the CPAP mask for providing padding between the mask seal and a wearer's nose bridge area to reduce the risk that bruising or ulcers will occur on the wearer's nose bridge area.

3. The padding of claim 2, wherein said exterior fabric material comprises a decorative soft outer surface.

4. The padding of claim 2, wherein edges of said end flaps and said long flaps are secured.

5. The padding of claim 2, wherein said nose bridge protector flap is attached to said forehead pad by stitching.

6. The padding of claim 2, wherein said nose bridge protector flap is of sufficient thickness and density to distribute pressure across the wearer's nose bridge area without compromising the seal against the wearer's face.

7. The padding of claim 2, wherein said nose bridge protector comprises:
   an upper end that tapers to a reduced width portion, and
   an enlarged terminal end depending downwardly from said reduced width portion, wherein said enlarged terminal end tucks into the mask seal of the CPAP mask so as to be captured in the mask seal.

8. A padding for a CPAP interface to cover a forehead part on a CPAP mask, said padding comprising:
a forehead pad comprising:
a forehead padding body formed from an exterior fabric material having a decorative side, said exterior fabric material having terminal ends that fold inwardly along folds and attach along edges to form pockets at distal ends of said forehead padding body and an opening therebetween to accommodate a forehead part of a CPAP mask, said exterior fabric material having slits cut along said folds to accommodate straps of the CPAP mask,
an interior padding layer within said pockets and extending therebetween, and
a nose bridge protector flap formed from a material having a decorative side, said nose bridge protector flap depending downwardly from said forehead padding, said nose bridge protector flap being sized and configured to tuck into a mask seal of the CPAP mask for providing padding between the mask seal and a wearer's nose bridge to reduce the risk that bruising and ulcers will occur.

9. The padding of claim 8, wherein said exterior fabric material and said nose bridge protector flap material comprise a decorative soft outer surface.

10. The padding of claim 2, wherein edges of said end flaps and said long flaps are secured.

11. The padding of claim 8, wherein said nose bridge protector flap is of sufficient thickness and density to distribute pressure across the wearer's nose bridge area without compromising the seal against the wearer's face.

12. The padding of claim 8, wherein said nose bridge protector comprises:
an upper end that tapers to a reduced width portion, and
an enlarged terminal end depending downwardly from said reduced width portion, wherein said enlarged terminal end tucks into the mask seal of the CPAP mask so as to be captured in the mask seal.

13. A combination, comprising:
a CPAP facial mask having a seal and straps for holding the seal against a wearer's face, the CPAP facial mask having a forehead part, and
a forehead pad covering said forehead part of said mask, said forehead pad comprising:
an exterior fabric material having distal ends, said exterior fabric material being folded along said distal ends and attach along edges to form pockets at said distal ends and an opening therebetween for attachment to said forehead part of said mask, said exterior fabric material further having slits in said distal ends where said exterior fabric material is folded, said straps of said mask extending through said slits, and
a padding layer, said folded exterior fabric material being folded around said padding layer so that said padding layer is within said exterior fabric material.

14. The combination of claim 13, wherein said exterior fabric material comprises a decorative soft outer surface.

15. The combination of claim 13, further comprising:
a downwardly depending nose bridge protector flap formed of a fabric material attached to a lower edge of the forehead pad along and extending between said pockets, said nose bridge protector flap being sized and configured to tuck into a mask seal of the CPAP mask for providing padding between the mask seal and a wearer's nose bridge area to reduce the risk that bruising or ulcers will occur on the wearer's nose bridge area.

16. The combination of claim 15, wherein said nose bridge protector flap is secured to said forehead pad.

17. The combination of claim 15, wherein said nose bridge protector flap is of sufficient thickness and density to distribute pressure across the wearer's nose bridge area without compromising the seal against the wearer's face.

18. The combination of claim 15, wherein said nose bridge protector comprises:
an upper end that tapers to a reduced width portion, and
an enlarged terminal end depending downwardly from said reduced width portion, wherein said enlarged terminal end tucks into the mask seal of the CPAP mask so as to be captured in the mask seal.

* * * * *